United States Patent
Wang

(10) Patent No.: US 11,466,049 B2
(45) Date of Patent: Oct. 11, 2022

(54) METHOD FOR PURIFYING CRUDE ROCURONIUM BROMIDE

(71) Applicant: JINAN GOOD MEDICAL TECHNOLOGY CO., LTD., Shandong (CN)

(72) Inventor: Jiawang Wang, Jinan (CN)

(73) Assignee: JINAN GOOD MEDICAL TECHNOLOGY CO., LTD., Jinan (CN)

( * ) Notice: Subject to any disclaimer, the term of this patent is extended or adjusted under 35 U.S.C. 154(b) by 0 days.

(21) Appl. No.: 17/261,281

(22) PCT Filed: Jul. 16, 2019

(86) PCT No.: PCT/CN2019/096224
§ 371 (c)(1),
(2) Date: Jan. 19, 2021

(87) PCT Pub. No.: WO2020/015659
PCT Pub. Date: Jan. 23, 2020

(65) Prior Publication Data
US 2021/0261601 A1  Aug. 26, 2021

(30) Foreign Application Priority Data
Jul. 20, 2018  (CN) .................. 201810804763.X

(51) Int. Cl.
*C07J 43/00* (2006.01)

(52) U.S. Cl.
CPC ................... *C07J 43/003* (2013.01)

(58) Field of Classification Search
CPC ...................................... C07J 43/003
See application file for complete search history.

(56) References Cited

U.S. PATENT DOCUMENTS

| | | | |
|---|---|---|---|
| 4,894,369 A | 1/1990 | Sleigh et al. | |
| 2006/0058275 A1 | 3/2006 | Friedman et al. | |
| 2014/0200340 A1 | 7/2014 | Zeng et al. | |
| 2020/0219060 A1 | 7/2020 | Fredericks et al. | |

FOREIGN PATENT DOCUMENTS

| | | |
|---|---|---|
| CN | 101381390 A | 3/2009 |
| CN | 101397329 A | 4/2009 |
| CN | 101993470 A | 3/2011 |
| CN | 103119051 A | 5/2013 |
| CN | 103435674 A | 12/2013 |
| CN | 103435675 A | 12/2013 |
| CN | 204115430 U | 1/2015 |
| CN | 105566433 A | 5/2016 |
| CN | 107312055 A | 11/2017 |
| EP | 2 703 408 A1 | 3/2014 |
| GB | 2 445 764 A | 7/2008 |

OTHER PUBLICATIONS

Oct. 16, 2019 Search Report issued in International Patent Application No. PCT/CN2019/096224.
Oct. 16, 2019 Written Opinion issued in International Patent Application No. PCT/CN2019/096224.
Li, Daitao "Study On Synthesis Process of Rocuronium Bromide and Related Substances", Master's Thesis of Shandong University. (2011). pp. 28?A50-A51,?Table 4-12.
Wang, Huixia, "Synthesis of High Purity Rocuronium Bromide.", Journal of Pharmacyand Clinical Research 21 (2), (2013), pp. 136-137.
Zhang, Shoushan, "Microwave Vacuum Dryer", Pharmaceutical Factory Workshop, (Oct. 31, 2005), pp. 1325-1328.
Jun. 8, 2020 Office Action issued in Chinese Patent Application No. 201810804763.X.
Fu, Chaomei et al., Pharmacy Experiment of Traditional Chinese Medicine, (2015), pp. 26-28.
Jul. 23, 2021 Extended European Search Report issued in European Patent Application No. 19838199.8.

*Primary Examiner* — Brenda L Coleman
(74) *Attorney, Agent, or Firm* — Oliff PLC

(57) ABSTRACT

A method for purifying crude rocuronium bromide includes removing the residual solvent in crude rocuronium bromide by vacuum microwave drying or fluidized drying to meet medicinal requirements. High-quality rocuronium bromide can be obtained by the method of the present application. The method makes the large-scale industrial production of rocuronium bromide easy to realize, and can also avoid or reduce the use of diethyl ether which is a flammable and explosive solvent. In addition, the equipment used requires less expense and occupies less space.

20 Claims, No Drawings

METHOD FOR PURIFYING CRUDE ROCURONIUM BROMIDE

BACKGROUND

Technical Field

The present invention relates to the field of medicine, and in particular to a method for purifying crude rocuronium bromide.

Related Art

Rocuronium bromide injection is a clinically widely used muscle relaxant. According to the guidelines of ICH (The International Council for Harmonization), the residual solvent in an active pharmaceutical ingredient (API) must be lower than a certain amount to meet the medicinal requirements. For example, for Class 2 solvents, the content of methylene chloride should not be higher than 600 ppm, the content of acetonitrile should not be higher than 410 ppm, and the content of methanol should not be higher than 3,000 ppm; for Class 3 solvents such as diethyl ether, methyl acetate, ethyl acetate and acetone, their content should not be higher than 5,000 ppm. Organic solvents are inevitably used in the production of rocuronium bromide, so the residual solvent in the raw rocuronium bromide material for medicinal use must meet the above requirements.

SUMMARY

The present application provides a method for purifying crude rocuronium bromide, by which a high-quality rocuronium bromide with a residual solvent that meets medicinal requirements can be obtained.

Generally, rocuronium bromide is synthesized by 7-9 steps of chemical reactions using epiandrosterone as a starting material. The detailed synthesis process can be found in the documents US20060058275A1, U.S. Pat. No. 4,894,369, US20050159398, CN201180045999.6, CN201610028808.X, CN200710092747.4, and GB 2445764. As can be seen from all current published literatures, although the first several steps may be different, these processes share the same final step: quaternization reaction between rocuronium bromide intermediate "monoester" (CAS No. 119302-24-8, (2β,3α,5α,16β,17β)-17-acetyloxy-3-hydroxy-2-(4-morpholine)-16-(1-pyrrolidyl)androstane) and 3-bromopropylene. The reaction equation is expressed as follows:

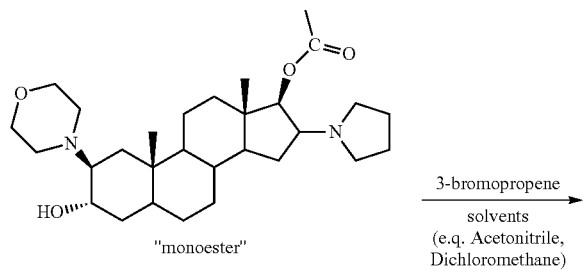

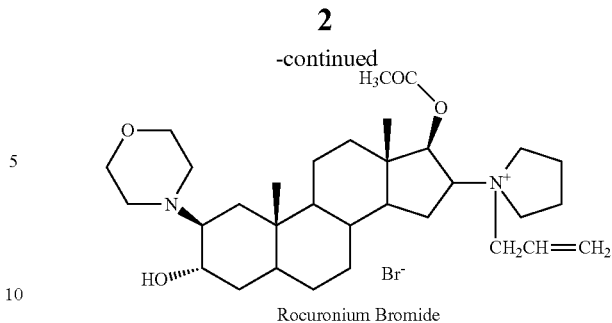

Rocuronium Bromide

The solvent used for the reaction is generally a dipolar aprotic solvent such as dichloromethane or acetonitrile; the reaction temperature is 10-40° C., and the reaction time is 5-24 hours. Those skilled in the art can adjust experimental parameters such as material ratio, reaction temperature, time, etc. according to actual conditions.

In the present application, crude rocuronium bromide refers to rocuronium bromide containing in which the content of organic solvent is higher than that required for use as an API during the preparation process of rocuronium bromide (API). The crude rocuronium bromide may be a solid-form rocuronium bromide containing a high content of residual solvent, may be in a slurry or paste form containing an excessively high content of residual solvent, or may refer to the reaction liquid of the final step of the synthesis process of rocuronium bromide.

Although rocuronium bromide injection has been clinically applied for more than 20 years, and there are a large number of reports on the synthesis process of rocuronium bromide (API) such as those mentioned above, up to now, there are still some difficulties in the industrial production of rocuronium bromide (API), and the existing production processes have still some defects. One of the main reasons is that the rocuronium bromide molecule and the solvents used in its manufacturing process will form solvates, and the solvents and the rocuronium bromide molecule in the solvates are strongly bonded, so the solvents are not easy to leave the rocuronium molecule. In order to remove the solvents from the solvates, the solvates must ordinarily be exposed to a very high temperature. However, rocuronium bromide is highly sensitive to heat and easily decomposes at a slightly high temperature, so removal of residual solvents from the crude rocuronium bromide to meet medicinal standards remains a major challenge to date.

There are mainly two methods for solving this problem: One is drying the crude rocuronium bromide containing diethyl ether as the main solvent under reduced pressure which is obtained by an anti-solvent crystallization. The anti-solvent crystallization herein is mixing the solution of rocuronium bromide in dichloromethane, acetonitrile or acetone or their mixture and with diethyl ether as the anti-solvent to get precipitate. In this case, the main residual solvent contained in the crude rocuronium bromide was diethyl ether which is a low-boiling flammable, explosive solvent. Another method is mixing rocuronium bromide solution and anti-solvent and crystallizing out the crude rocuronium bromide, dissolving the solid in a large amount of water, and reducing the residual solvent through freeze drying. In addition to diethyl ether, the anti-solvent used in the second method can also be other safer solvents with higher boiling points such as ethyl acetate, butyl acetate, hexane, heptane, methyl tert-butyl ether and the like.

The first method described above is use an anti-solvent to crystallize out a crude rocuronium bromide and then vacuum-dry it. In this case, only diethyl ether can be used as the anti-solvent, and other common solvents will not work. Although diethyl ether has a boiling point of only 36° C., diethyl ether and rocuronium molecules combine to form a solvate after precipitation of rocuronium bromide with diethyl ether as an anti-solvent; in order to make the residual diethyl ether reach the medicinal standard of 5,000 ppm or less, the vacuum drying must be carried out at 37° C. or higher under high vacuum level for a long time (generally at least 5 days, or even 10 days or more). However, rocuronium bromide easily decomposes and the impurities are obviously increased under this condition of drying, so the rocuronium bromide treated by this method will generally contain a high content of impurities even if the content is acceptable; and if the conditions of drying are not well controlled, for example, if the temperature is slightly higher or the drying time is slightly longer, the impurities are likely to rise to an unacceptable level.

A serious disadvantage of using diethyl ether is that diethyl ether is very flammable and explosive. Therefore, although diethyl ether is not completely prohibited in the production of APIs, it is generally used only when the used amount is small and there is no other solvent available. However, if rocuronium bromide is produced by anti-solvent crystallization with diethyl ether, the amount of diethyl ether employed is rather large. For example, if 10 kg of rocuronium bromide is used, 1,100 L or more of diethyl ether is usually required, so there is a serious safety hazard in the production process. In addition, medicinal rocuronium bromide (API) should be produced in a closed clean area according to GMP requirements, which further increases the risk level. For safety reasons, projects that use a large amount of ether are often not approved by the regulatory authority especially when EHS (environmental, safety, health) requirements are becoming more stringent.

According to the literature US Patent No. US20060058275A1 and the previous research results of the inventors, the solvent with a slightly high boiling point which can be used in the production of rocuronium bromide, such as dichloromethane, n-hexane, methyl acetate, ethyl acetate, butyl acetate, isobutyl ethyl ester, methyl tert-butyl ether, etc. will be combined with rocuronium bromide to form a solvate, which cannot be removed by the conventional vacuum drying method to meet the medicinal standards. If the solvent used in the final step of the production process of the rocuronium bromide is methyl tert-butyl ether or ethyl acetate, the crude rocuronium bromide will contain the residual solvent methyl tert-butyl ether or ethyl acetate. Even if after dried at 80° C. and −0.098 Mpa for 16 hours, the crude product still contains a high level of tert-butyl ether or ethyl acetate, which still greatly exceeds the upper limit of 5,000 ppm stipulated in the standards, and sometimes may even be 100 times greater than the upper limit, i.e., reach 500,000 ppm or higher. Drying under these conditions for another 12 hours basically will not lower the content of methyl t-butyl ether or ethyl acetate.

In the second method mentioned above, safer solvents having higher boiling points (for example, ethyl acetate, butyl acetate, methyl tert-butyl ether, etc.) can be used as the anti-solvent to crystallize rocuronium bromide from the solution, and then freeze drying is performed to remove such solvents that remain in the crude rocuronium bromide. Although the solvent in the crude rocuronium bromide can be removed to meet the medicinal standards by the freeze-drying method as described in the literatures CN200710092747.4, GB 2445764, and US20060058275A1, the obtained rocuronium bromide usually contains a high content of an impurity C, which is difficult to be controlled below 0.1%, is generally close to 0.2%, which is the upper limit stipulated in EP8.0 (European Pharmacopeia 8.0), and may easily exceed 0.2% if not carefully controlled. The reason is that rocuronium bromide is an acetate which is easily hydrolyzed in the presence of water, the freeze drying operation requires first dissolving the crude rocuronium in a large amount of water, and the content of the impurity C increases due to hydrolysis. In addition, the freeze drying method requires high energy consumption, large space for equipment, and large equipment investment. Under the same production scale, the equipment investment of the freeze drying method is 10 times higher than that of the method of present application.

Therefore, at present, it is quite difficult to remove the solvent contained in the crude rocuronium bromide to make the content of the residual solvent contained in the final product reach an acceptable limit for drug use, which is a difficulty in the manufacturing of rocuronium bromide. That is to say, after obtaining the above-mentioned "crude rocuronium bromide", it is very difficult to remove the solvent therein to obtain the pharmaceutically acceptable rocuronium bromide (API).

Based on this, the present application provides a method for purifying crude rocuronium bromide which includes removing the residual solvent in the crude rocuronium bromide by vacuum microwave drying method or fluidized drying method to meet medicinal requirements. The method not only overcomes the difficulties as described above, but also has simple operation, environmental friendliness, low cost and significant effects.

Further, in one or more embodiments of the present application, the method includes replacing the residual solvent in the crude rocuronium bromide with a solvent A and then vacuum microwave drying the crude rocuronium bromide containing the solvent A.

Further, in one or more embodiments of the present application, the method includes: mixing the solvent A and crude rocuronium bromide into a liquid containing rocuronium bromide, solidifying the liquid by vacuum microwave (vacuum microwave solidification), and then treating by vacuum microwave drying and/or other drying methods to make the contents of solvent and water contained therein meet medicinal requirements.

The vacuum microwave solidification described herein means that the liquid material treated by vacuum microwave turns into a solid due to evaporation of the solvent after the vacuum microwave drying is carried out to a certain extent. The content of the residual solvent in the rocuronium bromide sample at the beginning of solidification is generally higher than that required by the medicinal standards. In this case, vacuum microwave drying and/or other drying methods are required for further treatment.

Further, the solvent A is a polar solvent with strong microwave absorption ability. It may be further selected from one or more of a $C_1$ to $C_4$ monohydric alcohol, a $C_1$ to $C_3$ monobasic acid, acetone, methyl ethyl ketone, tetrahydrofuran and water. Of course, in practice, the solvent A is not limited thereto, and those skilled in the art can select or try other feasible solvents while using the present invention according to the disclosure of the present application, and it should be known that such simple selection of solvents is a conventional option based on the present invention, which shall also fall within the scope of protection of the present application.

In some embodiments, the solvent A described herein is selected from one or more of a $C_1$ to $C_3$ monohydric alcohol, a $C_1$ to $C_3$ monobasic acid, acetone, methyl ethyl ketone, tetrahydrofuran, and water.

In some embodiments, the solvent A is selected from one or more of methanol, ethanol, isopropanol, a $C_1$ to $C_3$ monobasic acid, acetone, methyl ethyl ketone, tetrahydrofuran, and water.

In some embodiments, the solvent A is selected from one or more of methanol, ethanol, a $C_1$-$C_3$ monobasic acid, acetone, butylketone, tetrahydrofuran and water. Or, in some embodiments, the solvent A is selected from one or more of methanol, a $C_1$-$C_3$ monobasic acid, acetone and water. Or, in some embodiments, the solvent A is selected from one or more of a $C_1$-$C_3$ monohydric alcohol, formic acid, acetic acid, acetone and water. Or, in some embodiments, the solvent A is selected from one or more of methanol, ethanol, formic acid, acetic acid, propionic acid, acetone and water. Or, in some embodiments, the solvent A is selected from one or more of methanol, ethanol, isopropanol, formic acid, acetic acid, acetone and water. Or, in some embodiments, the solvent A is selected from one or more of methanol, ethanol, formic acid, acetic acid and water. Or, in some embodiments, the solvent A is selected from one or more of methanol, formic acid, acetic acid, acetone and water. Or, in some embodiments, the solvent A is selected from one or more of methanol, formic acid, acetic acid, acetone and water. Or, in some embodiments, the solvent A is selected from one or more of methanol, ethanol, acetic acid, acetone and water. Or, in some embodiments, the solvent A is selected from one or more of methanol, formic acid, acetone and water. Or, in some embodiments, the solvent A is selected from one or more of methanol, formic acid, or water. Or, in some embodiments, the solvent A is selected from one or more of methanol, acetic acid, or water. Or, in some implementation methods, the solvent A is methanol, ethanol, methanol and water (methanol/water or methanol-water), ethanol and water (ethanol/water or ethanol-water), methanol and water and acetic acid (methanol/water/acetic acid or methanol-water-acetic acid), or ethanol and water and acetic acid (ethanol/water/acetic acid or ethanol-water-acetic acid)

Further, in some embodiments, rocuronium bromide is unstable and easily hydrolyzed in the presence of water, which can be stabilized by adding acetic acid. However, acetic acid is difficult to remove due to its high boiling point and cannot be completely removed from the product. Therefore, the amount of acetic acid added must be properly controlled to ensure that the content of acetic acid in the final purified rocuronium bromide product does not exceed the upper limit of 5% (mass percentage, w/w: i.e. 100 g of rocuronium bromide (API) contains no more than 5 g of acetic acid) stipulated in the USP38 (United States Pharmacopoeia 38) standard or meets other special requirements.

Further, in some embodiments of the present application, considering the fact that after the acetic acid is added, a part of the acetic acid is volatilized during the subsequent treatment process, the amount of acetic acid added may exceed 5% (V/V), but generally does not exceed 8% (V/V) of the total amount of the solvent A, so as to further control the content of acetic acid in the final product to not exceed the upper limit of 5% (W/W) stipulated in the USP standard.

Further, in one or more embodiments of the present application, the vacuum microwave has a vacuum level of −0.01 to −0.1 Mpa; or further −0.01 to −0.099 Mpa, further −0.01 to −0.08 Mpa, further −0.01 Mpa to −0.07 Mpa, or further −0.01 Mpa to −0.06 Mpa; or further −0.06 Mpa to −0.1 Mpa, further −0.06 Mpa to −0.099 Mpa, further −0.06 Mpa to −0.09 Mpa, further −0.06 Mpa to −0.089 Mpa, further −0.06 Mpa to −0.08 Mpa, further −0.06 Mpa to −0.079 Mpa, or further −0.06 Mpa to −0.07 Mpa; or further −0.07 Mpa to −0.1 Mpa, further −0.07 Mpa to −0.099 Mpa, further −0.07 Mpa to −0.09 Mpa, further −0.07 Mpa to −0.089 Mpa, or further −0.07 Mpa to −0.08 Mpa; or further −0.08 Mpa to −0.099 Mpa (for example, −0.08 Mpa to −0.096 Mpa, or −0.08 Mpa to −0.098 Mpa), further −0.08 Mpa to −0.09 Mpa, further −0.08 Mpa to −0.089 Mpa, or further −0.08 Mpa to −0.085 Mpa.

Further, in one or more embodiments of the present application, the temperature of the vacuum microwave is 10-60° C., and may be, for example, 10° C., 15° C., 20° C., 25° C., 30° C., 35° C., 40° C., 45° C., 50° C., 55° C. or 60° C.; or further 10-50° C. or 20-50° C.; or further 10-40° C. or 20-40° C., or further 30-40° C., or further 25-36° C. The definition of the temperature herein applies to the temperature range, for example, below 43° C., below 40° C., or below 36° C. as described in the embodiments of the present application.

Further, the other drying methods may be those commonly employed by those skilled in the art, or may be selected from one or more of a vacuum drying method, a gas blow-drying method, and a fluidized drying method. However, the present application is not limited thereto, and it should be known that those of ordinary skill in the art have the ability to select other drying methods in accordance with the method of the present application based on the disclosure of the present application.

The gas blow-drying method described in the present application is placing a solid material in a sealed device allowing for the intake and exhaust of gas, maintaining the device at a certain temperature, and allowing air or inert gas to enter and exit the device. For example, the method can be putting the solid material in a tray on a deck of a vacuum oven, maintaining the vacuum oven at a certain temperature, and allowing air or inert gas to enter and exit the vacuum oven. Preferably, inert gas is used, especially when the water content of the material is high, because air may oxidize the product and change the color of the product.

Further, in one or more embodiments of the present application, the method includes: 1) mixing the solvent A and crude rocuronium bromide into a liquid containing rocuronium bromide, 2) solidifying the liquid by vacuum microwave (vacuum microwave solidification), and 3) then treating by vacuum microwave drying and/or gas blow-drying method to make the contents of solvent and water meet medicinal requirements.

Further, in some embodiments, after the content of the residual solvent has reached the medicinal requirements, vacuum drying can be continued without gas introduction to remove water.

Further, in some embodiments, the crude rocuronium bromide may be vacuumed in a vacuum oven prior to vacuum microwave drying.

Further, in one or more embodiments of the present application, when the vacuum microwave drying is carried out to a certain extent, the crude rocuronium bromide is solidified, and the crude rocuronium bromide solid still contains residual solvent and water. If the requirements of the medicinal standards are not met, the vacuum microwave drying may be continued, or a gas blow-drying method, a vacuum drying method, a fluidized drying method, or a combination thereof may be adopted. The gas blow-drying method described herein is placing a solid material in a sealed device allowing for the intake and exhaust of gas, maintaining the device at a certain temperature, and allowing air or inert gas to enter and exit the device. For example, the method can be putting the solid material in a tray on a deck of a vacuum oven, maintaining the vacuum oven at a certain temperature, and allowing air or inert gas to enter and exit the vacuum oven.

According to the embodiments of the present application, the liquid obtained by mixing the crude rocuronium bromide and the solvent A with high microwave-absorbing ability can be solidified by vacuum microwave drying at a low temperature (for example, 10-60° C. in some embodiments, or 20-40° C. in some embodiments, or 25-36° C. in some other embodiments) for a short period of time (for example, in some embodiments, for 10-25 min, or further 10-20 min, such as 10 min, 12 min, 14 min, 15 min, 16 min, 17 min, 18 min, 19 min, 20 min, 23 min, and 25 min), followed by vacuum microwave drying to make the solvent meet the medicinal standards. After the solid is obtained, it can also be treated by other drying methods (for example, one or more of gas blow-drying, vacuum drying, and fluidized drying) to make the residual solvent contained therein meet the standards for APIs.

Further, in some embodiments of the present application, if other drying methods are used after vacuum microwave solidification, the temperature used in the other drying methods shall not exceed 60° C., generally not exceed 43° C., and further not exceed 36° C.

Further, if the production scale is not too large, the solid obtained by vacuum microwave solidification can be transferred into a small vacuum drying box (such as DZF-6050 vacuum drying oven) for subsequent gas blow-drying; if the production scale is relatively large, a large vacuum drying oven or double cone rotary dryer for industrial use can be used for gas blow-drying. During the drying process, the temperature inside the box (material) is kept at a certain level (generally 26-43° C.), and nitrogen, argon, carbon dioxide or air is introduced for gas blow-drying. Alternatively, vacuum drying may be used, or gas blow-drying and vacuum drying may be used in combination. In some embodiments of the present application, the effect of solvent removal can be increased by maintaining the humidity of the material or system at a certain level.

According to an embodiment of the present application, the power of the vacuum microwave may be adjusted according to the amount of the material to be dried, the pumping rate of the pump during drying and/or a maximum vacuum level of the vacuum microwave, and the progress of the drying process. In general, some embodiments of the present application require high power at the early stage of the drying process due to the high solvent content, and low power at the later stage due to the low solvent content.

According to one or more embodiments of the present application, when 200 g of material is dried at a time, the power of the microwave varies from 300 W to 800 W; and when 6-8 kg of the material is dried at a time, the power of the microwave varies from 1,000 W to 20,000 W.

In one or more embodiments of the present application, the method includes fluidizing drying a crude rocuronium bromide in which diethyl ether is the main residual solvent.

The crude rocuronium bromide in which diethyl ether is the main residual solvent in the present application is a crude rocuronium bromide containing diethyl ether as the main residual solvent, or a crude rocuronium bromide containing diethyl ether as the main residual solvent, which is obtained after treating the crude rocuronium bromide defined above.

In the present application, that diethyl ether is the main residual solvent refers to that the content of diethyl ether as the residual solvent exceeds the medicinal standards, and the contents of other residual solvents have met or almost met the requirements. For example, if the residual solvents contained are diethyl ether and dichloromethane, the amount of diethyl ether should be no more than 5,000 ppm and the amount of dichloromethane should be no more than 600 ppm according to the ICH (the International Council for Harmonization) guidelines. That diethyl ether is the main residual solvent as described herein means that the amount of diethyl ether is more than 5,000 ppm, and may even be 100 times higher than 5,000 ppm, i.e., 500,000 ppm, and the amount of dichloromethane is less than 600 ppm or close to 600 ppm, for example, is 610 ppm or 620 ppm.

Further, in one or more embodiments of the present application, the crude rocuronium bromide in which diethyl ether is the main residual solvent as described in the present application is a crude rocuronium bromide containing diethyl ether as the main residual solvent, which is obtained after treating the crude rocuronium bromide defined above by anti-solvent crystallization.

In some embodiments of the present application, the method includes treating the crude rocuronium bromide by an anti-solvent crystallization method so that the crude rocuronium bromide contains diethyl ether as a main residual solvent, followed by fluidized drying.

In some embodiments of the present application, the anti-solvent crystallization method includes dissolving crude rocuronium bromide in a solvent B to prepare a crude rocuronium bromide solution, and mixing the crude rocuronium bromide solution with a solvent C to prepare a crude rocuronium bromide solid.

Further, in one or more embodiments of the present application, the solvent B is a dipolar aprotic solvent; further, the solvent B is a solvent capable of dissolving rocuronium bromide. Further, the solvent B is selected from one or more of dichloromethane, acetonitrile, acetone, dimethyl sulfoxide (DMSO), N,N-dimethylformamide (DMF) and N,N-dimethylacetamide. Further, the solvent B is selected from one or more of dichloromethane, acetonitrile, acetone, and DMSO. Further, the solvent B is dichloromethane.

Further, in one or more embodiments of the present application, the solvent C is an anti-solvent, and further, is a solvent in which rocuronium bromide is insoluble or slightly soluble. Further, the solvent C is diethyl ether or a solvent other than diethyl ether. Further, the solvent other than diethyl ether is selected from one or more of isopropyl ether, methyl tert-butyl ether, methyl acetate, ethyl acetate, butyl acetate, propyl acetate, cyclohexane, n-hexane, and n-heptane. Further, the solvent other than diethyl ether is selected from one or more of methyl tert-butyl ether, methyl acetate, ethyl acetate and n-hexane. Further, the solvent other than diethyl ether is methyl tert-butyl ether, methyl acetate, ethyl acetate or n-hexane.

Further, in one or more embodiments of the present application, the method includes dissolving crude rocuronium bromide in the solvent B to prepare a crude rocuronium bromide solution, and mixing the crude rocuronium bromide solution and the solvent C to obtain a crude rocuronium bromide solid, followed by fluidized drying.

Further, in some embodiments, when the solvent C is diethyl ether, the method includes dissolving crude rocuronium bromide in the solvent B to prepare a crude rocuronium bromide solution, mixing the crude rocuronium bromide solution and the solvent C to obtain a crude rocuronium bromide solid, followed by fluidized drying.

Further, in the practice of the present application, diethyl ether in the crude rocuronium bromide can be relatively easily removed by fluidized drying, but it is difficult to remove other solvents in the crude rocuronium bromide (such as ethyl acetate, methyl acetate, n-hexane, methyl tert-butyl ether, etc.). Therefore, during the implementation of the present application, if the crude rocuronium bromide solid is prepared by using the above other solvent C as an anti-solvent in consideration of the danger of diethyl ether, the filtered solid that is precipitated from these anti-solvents (solvent C) with high boiling point may be washed with diethyl ether so that before fluidized drying, diethyl ether is the main solvent contained in the crude rocuronium bromide and the contents of other solvents are close to or reach the upper limits stipulated in the medicinal standards. This will reduce the amount of diethyl ether used.

Further, in some embodiments, when the solvent C is not diethyl ether, the method includes dissolving crude rocuronium bromide in the solvent B to prepare a crude rocuronium bromide solution, mixing the crude rocuronium bromide solution and the solvent C to prepare a crude rocuronium bromide solid, and washing the solid with diethyl ether, followed by fluidized drying.

In one or more embodiments of the present application, the fluidized drying described in the present application is also called "boiling drying". The equipment used includes a fluidized bed dryer (such as XF series boiling dryer XF10, XF20, XF30, etc.), a vibrating fluidized bed dryer (such as ZLG series vibrating fluidized bed dryer), and so on. In such a drying method, a material (generally powdery or finely granulated) is placed on a ventilated sieve plate, and the gas passes through the sieve plate at a certain velocity from the lower part of the sieve plate, to blow the material up into a fluidized or boiling state. The material particles moving up and down in the gas flow collide with each other and are thus fully mixed, so the drying efficiency is high. The gas passing through the dried material will leave after dust carried in the material is removed by a cloth bag or a cyclone. The dried product will be discharged from the discharge port after being qualified.

Further, in one or more embodiments, the gas used for fluidized drying in the present application may be inert gas (such as nitrogen, carbon dioxide, or argon) or air. Further, in the case of air, drying and purification treatment are generally required. When air with too much water comes into contact with the rocuronium bromide solid (such as powder), it not only hydrolyzes rocuronium bromide, but also may cause agglomeration of the rocuronium bromide, resulting in a poor drying effect. The drying and purifying treatment may be implemented by passing the air through a concentrated sulfuric acid gas-washing bottle, an alkali lime tower and so on. Further, in one or more embodiments of the present application, the temperature used for the above mentioned drying treatment is 15-70° C., for example, 15° C., 20° C., 25° C., 30° C., 35° C., 40° C., 45° C., 50° C., 55° C., 60° C., 65° C. or 70° C.; or further 15-60° C., still further 15-50° C. or 25-50° C., and yet further 30-37° C.

In the present application, the flow rate of the gas flow in the fluidized drying method is not particularly limited, but is preferably large enough to keep the material in a sufficiently fluidized state, thereby ensuring sufficient contact between the material and the gas, to cause frictional collision between the materials so that the solvent is taken away as soon as possible. Low gas flow rates will greatly extend the time required for removing the solvent.

As described above, in one or more embodiments of the present application, if solvents C other than diethyl ether are used (where the solvent C other than diethyl ether may be that described above, for example, ethyl acetate, methyl acetate, n-hexane, methyl tert-butyl ether, etc.) as anti-solvents, it is difficult to remove these solvents C with high boiling points subsequently by fluidized drying to meet medicinal requirements. Therefore, these solvents C with high boiling points must be washed away with diethyl ether before the subsequent fluid drying is carried out.

Further, as another option, in one or more embodiments of the present application, when the solvent C is not diethyl ether, the method includes dissolving crude rocuronium bromide in the solvent B to prepare a crude rocuronium bromide solution, mixing the crude rocuronium bromide solution with the solvent C to prepare a crude rocuronium bromide solid, mixing the crude rocuronium bromide solid with a solvent A to form a liquid containing rocuronium bromide, and then vacuum microwave drying the liquid. In some embodiments, the content of the solvent other than diethyl ether may be first reduced to a certain extent by vacuum concentration or gas blowing before the vacuum microwave drying.

Further, in some embodiments, the method includes dissolving crude rocuronium bromide in the solvent B to prepare a crude rocuronium bromide solution, mixing the crude rocuronium bromide solution with the solvent C to prepare a crude rocuronium bromide solid, mixing the crude rocuronium bromide solid with the solvent A to form a liquid containing rocuronium bromide, solidifying the liquid by vacuum microwave drying, and then treating by vacuum microwave drying and/or other drying methods to make the contents of residual solvents and water meet medicinal requirements. In some embodiments, the content of the solvent other than diethyl ether may be first reduced to a certain extent by vacuum concentration or gas blowing before the vacuum microwave drying.

Further, the solvent A is selected as described above. For example, in some embodiments of the present application, the solvent A may be selected from one or more of methanol, ethanol, water, isopropanol, butanol, acetone, methyl ethyl ketone, tetrahydrofuran, formic acid, acetic acid and propionic acid, and may further be selected from one or more of methanol, acetic acid, formic acid, water, and acetone.

Further, in some embodiments, rocuronium bromide is unstable and easily hydrolyzed in the presence of water, which can be stabilized by adding acetic acid. However, acetic acid is difficult to remove due to its high boiling point and cannot be completely removed from the product. Therefore, the amount of acetic acid added must be properly controlled to ensure that the content of acetic acid in the final purified rocuronium bromide product does not exceed the upper limit of 5% (mass percentage, w/w: i.e. 100 g of rocuronium bromide (API) contains no more than 5 g of acetic acid) stipulated in the USP38 (United States Pharmacopoeia 38) standard or meets other special requirements.

Further, in some embodiments of the present application, considering the fact that after the acetic acid is added, a part of the acetic acid is volatilized during the subsequent treatment process, the amount of acetic acid added may exceed 5% (V/V), but generally does not exceed 8% (V/V) of the total amount of the solvent A, so as to further control the content of acetic acid in the final product to not exceed the upper limit of 5% (W/W) stipulated in the USP standard.

Further, in one or more embodiments of the present application, when the vacuum microwave drying is carried out to a certain extent, the crude rocuronium bromide will be solidified, and the crude rocuronium bromide solid still contains residual solvent and water. If the requirements of the medicinal standard are not met, the vacuum microwave drying may be continued, or the gas blow-drying method, the vacuum drying method, the fluidized drying method, or the comprehensive utilization of such methods may be selected. The gas blow-drying method described herein is placing a solid material in a sealed device allowing for the intake and exhaust of gas, maintaining the device at a certain temperature, and allowing air or inert gas to enter and exit the device. For example, the method can be putting the solid material in a tray on a deck of a vacuum oven, maintaining the vacuum oven at a certain temperature, and allowing air or inert gas to enter and exit the vacuum oven.

According to the embodiments of the present application, the liquid obtained by mixing the crude rocuronium bromide and the solvent A with high microwave-absorbing ability can be solidified by vacuum microwave drying at a low temperature (for example, 10-60° C. in some embodiments, or 20-40° C. in some embodiments, or 25-36° C. in some embodiments) for a short period of time (for example, in some embodiments, for 10-25 min, or further 10-20 min, such as 10 min, 12 min, 14 min, 15 min, 16 min, 17 min, 18 min, 19 min, 20 min, 23 min, or 25 min), followed by vacuum microwave drying to make the solvent meet medicinal standards. After the solid is obtained, it can also be treated by other drying methods (for example, airflow blowing, vacuum drying, and fluidized drying) to make the residual solvent contained therein meet the standards for APIs.

Further, in some embodiments of the present application, if other drying methods are used after vacuum microwave solidification, the temperature used in the other drying methods shall not exceed 60° C., generally not exceed 43° C., and further not exceed 36° C.

Further, if the production scale is not too large, the solid obtained by vacuum microwave solidification can be transferred into a small vacuum drying box (such as DZF-6050 vacuum drying oven) for subsequent gas blow-drying; if the production scale is relatively large, a large vacuum drying oven or double cone rotary dryer for industrial use can be used for gas blow-drying. During the drying process, the temperature inside the box (material) is kept at a certain level (generally 26-43° C.), and nitrogen, argon, carbon dioxide or air is introduced for gas blow-drying. Alternatively, vacuum drying may be used, or gas blow-drying and vacuum drying may be used in combination. In some embodiments of the present application, the effect of solvent removal can be increased by maintaining the humidity of the material or system at a certain level.

In some embodiments of the present application, the vacuum level of vacuum microwave drying and the temperature of vacuum microwave drying may be as described above. For example, the vacuum level of vacuum microwave drying is −0.01 Mpa to −0.1 Mpa, or further −0.06 Mpa to −0.1 Mpa in some embodiments, or further −0.08 Mpa to −0.099 Mpa in some embodiments. For example, the temperature of vacuum microwave drying may be 10-60° C. in some embodiments, or further 20-60° C. in some embodiments, or further 20-40° C. in some embodiments, or further 30-40° C. in some embodiments, or further 25-36° C. in some embodiments.

According to an embodiment of the present application, the power of the vacuum microwave may be adjusted according to the amount of the material to be dried, the pumping rate of the pump during drying and/or a maximum vacuum level of the vacuum microwave, and the progress of the drying process. In general, some embodiments of the present application require high power at the early stage of the drying process due to the high solvent content, and low power at the later stage due to the low solvent content.

According to one or more embodiments of the present application, when 200 g of material is dried at a time, the power of the microwave varies from 300 W to 800 W; and when 6-8 kg of the material is dried at a time, the power of the microwave varies from 1,000 W to 20,000 W.

The purification method of the present application basically does not destroy the structure of rocuronium bromide molecule during the process of removing the residual solvent. When the content of the related substances in the crude rocuronium bromide is not high, the contents of the related substances in the purified rocuronium bromide product obtained by the vacuum microwave drying method and the subsequent drying treatment of the present application are generally relatively low. In some embodiments of the present application, the content of impurity A is found to decrease after the purification is completed.

After the crude rocuronium bromide is purified according to the method of the present application, high-quality rocuronium bromide (finished product) is obtained, where the related substances (known impurities) and their contents thereof and the content of the residual solvents in the finished product meet the requirements of EP 8.0 and/or USP 38. In most cases, the contents of the related substances may be 0.1% or below, and the total content of known and unknown impurities is generally no more than 0.4%. The content of the main product rocuronium bromide is 99.0% or more as analyzed according to the USP standards (where the content stipulated in the USP standards is 98-102%); and other quality indicators are also satisfactory and meet the medicinal standards.

High-quality rocuronium bromide can be obtained by the method of the present application. The method makes the large-scale industrial production of rocuronium bromide easy to realize, and can also avoid or reduce the use of diethyl ether which is a flammable and explosive solvent. In addition, the production equipment requires less expense and occupies less space.

DETAILED DESCRIPTION

The present invention will be further described below with reference to specific embodiments. It should be understood that these examples are only used to illustrate the present invention and not to limit the scope of the present invention. The experimental methods without specific conditions in the following examples are usually in accordance with conventional conditions or conditions recommended by equipment manufacturers.

Unless otherwise defined, all professional and scientific terms used herein have the same meanings as those familiar to those skilled in the art.

The following examples 1-7 are merely used as exemplary embodiments for the purpose of enabling those skilled in the art to understand the technical solutions of the present application more clearly. However, the present application only provides a completely new method that can be used as a guide. The technical solutions as below all fall within the scope of the present application: 1) the same or similar technical means as the following embodiments of the present application, 2) or the technical solutions mentioned in the abstract of the present invention, 3) or the technical solutions that are obvious or similar to the content of the present application, 4) or the technical means of implementing the present application by using the solvents or operations or parameters commonly used by those skilled in the art according to the instructions of the present application, 5) or technical solutions obtained by combining two or more of the above or obtained by simply replacing one or more conventional techniques with a combination of technical means. In addition, as previously stated, the present application presents a completely new method which is intended to provide guidance; therefore, it should be understood that all the modes of implementation of the present application cannot be enumerated in an exhaustive manner.

The crude rocuronium bromide in the following examples can be prepared with reference to the methods described in US and Chinese Patents No. US20060058275A1, CN101381390A or U.S. Pat. No. 4,894,369 or modifications thereof. For the determination of impurities, content and acetic acid, see the standards for rocuronium bromide in USP38. For the analysis of residual solvents, see US Patent No. US20060058275A1 (paragraph 0077-0079). The Karl Fischer method was used for water determination.

The guidelines of USP 38 and ICH (the International Council for Harmonization) are as follows:

According to the standard for rocuronium bromide in USP 38, the related substances are as follows: A≤0.2%, B≤0.3%, C≤0.3%; D≤0.1%, E≤0.1%, F≤0.1%, G≤0.1%, H≤0.1%, total amount of impurities ≤1.5%, acetic acid ≤5%; content: 98-102%

According to the ICH guidelines, the requirements on the residual solvents are as follows: dichloromethane ≤600 ppm, acetonitrile ≤410 ppm, ethanol ≤5,000 ppm, methanol ≤3,000 ppm, methyl tert-butyl ether ≤5,000 ppm, and ethyl acetate ≤5,000 ppm.

Example 1

Preparation of crude rocuronium bromide: 500 g of rocuronium bromide intermediate monoester, 2.25 L of dichloromethane, and 600 mL of 3-bromopropene were mixed and stirred at room temperature for 16 hours. The reaction mixture was filtered and diluted with 1.75 L of dichloromethane, and was then mixed with 25 L of methyl tert-butyl ether while stirring vigorously, which gave a suspension containing a white precipitate. After the suspension was stirred for 20 minutes, the precipitate was filtered off, then re-dissolved with 3.5 L of dichloromethane, and added to 25 L of methyl tert-butyl ether under stirring. The precipitate was filtered off and washed with methyl tert-butyl ether to obtain crude rocuronium bromide.

Purifying of crude rocuronium bromide: firstly, the above crude rocuronium bromide was vacuumed in a vacuum oven for 3-5 hours, and then transferred to a 2 L single-necked flask. 680 mL of methanol, 100 mL of water and 30 mL of acetic acid were added to the flask. The solid was dissolved by bubbling with nitrogen, and added to a microwave tray which was then placed in a microwave vacuum dryer for vacuum microwave drying. The temperature was controlled below 43° C., and the vacuum level was −0.08 Mpa to 0.096 Mpa. After about 16 min of the vacuum microwave drying, a solid was obtained. The solid continued to be dried at a temperature of no more than 43° C. and a vacuum level of higher than −0.096 Mpa for another 50-60 min. The contents of residual solvent and water in the material were tracked and monitored. After the contents of the residual solvents and water were qualified, the material was taken out to obtain a purified rocuronium bromide.

Analysis: water 2.6%; the contents of residual solvents: methanol 2,800 ppm, dichloromethane 60 ppm, methyl tert-butyl ether 2,960 ppm, and acetic acid 4.6%; related substances: A 0.11%, C 0.10%, F 0.07%, G 0.03%, H 0.05%, B, D, and E were not detected, and the total amount of impurities was 0.4% (the upper limit of the qualification standard was 1.5%); and the content was 99.1% (calculated on the anhydrous and acetic acid-free basis).

Example 2

Preparation of crude rocuronium bromide: 500 g of rocuronium bromide intermediate monoester, 2 L of acetonitrile and 600 mL of 3-bromopropene were mixed and stirred at room temperature for 8 hours. The reaction mixture was filtered and diluted with 2 L of dichloromethane, and was then mixed with 25 L of methyl tert-butyl ether while stirring vigorously, which gave a suspension containing a white precipitate. After the suspension was stirred for 20 minutes, the precipitate was filtered off, then re-dissolved with 3.5 L of dichloromethane, and added to 25 L of methyl tert-butyl ether under stirring. The precipitate was filtered off and washed with methyl tert-butyl ether to obtain crude rocuronium bromide.

Purifying of the crude rocuronium: firstly, the crude rocuronium bromide was vacuumed in a vacuum oven for 30 minutes, and then transferred to a 2 L single-necked flask. 560 mL of methanol was added to the flask. The solid was dissolved by bubbling with carbon dioxide gas with a conduit to form a homogeneous liquid, and then 60 mL of water was added to the flask. The bubbling continued for another 1 hour. The liquid in the flask was poured into a microwave tray which was then placed in a microwave vacuum dryer for vacuum microwave drying. The temperature was controlled below 36° C., and the vacuum level was −0.08 Mpa to 0.096 Mpa. A solid was obtained after about 20-23 min of the vacuum microwave drying.

The solid was transferred to another vacuum drying oven with a temperature of 34-37° C. After carbon dioxide gas was passed into and out of the vacuum drying oven for about 24 hours, sampling and determination of the content of residual solvent were performed. When the residual solvent methanol was not higher than 3,000 ppm, the gas blowing was stopped, the vacuum drying oven was connected to a vacuum pump and vacuumed (to make the vacuum level higher than −0.095 Mpa) for further drying (with phosphorus pentoxide placed in the oven). After about 6 hours, the material was taken out, which is the purified rocuronium bromide.

Analysis: water content 2.1%; the contents of residual solvents: methanol 2,090 ppm, acetonitrile: not detected, methyl tert-butyl ether 2,350 ppm, and dichloromethane 330 ppm; related substances: A 0.06%, C 0.09%, F 0.05%, G 0.02%, H 0.04%, B, D, and E were not detected, and the total amount of impurities was 0.36% (the upper limit of the qualification standard was 1.5%); and the content was 99.3% (calculated on the anhydrous basis).

Example 3

Preparation of crude rocuronium bromide: 500 g of rocuronium bromide intermediate monoester, 2 L of acetonitrile and 600 mL of 3-bromopropene were mixed and stirred at room temperature for 8 hours. The reaction mixture was filtered and diluted with 2 L of dichloromethane, and was then mixed with 25 L of methyl tert-butyl ether while stirring vigorously, which gave a suspension containing a white precipitate. After the suspension was stirred for 20 minutes, the precipitate was filtered off, then re-dissolved with 3.5 L of dichloromethane, and added to 25 L of methyl tert-butyl ether under stirring. The precipitate was filtered off and washed with methyl tert-butyl ether to obtain a crude rocuronium bromide.

Purifying of the crude rocuronium: the crude rocuronium bromide was added to a 2 L single-necked flask. A mixture of 480 mL of methanol and 100 mL of water was added to the flask. The solid was dissolved by bubbling with carbon dioxide gas and stirring to form a homogeneous liquid. The liquid in the flask was poured into a microwave tray which was then placed in a microwave vacuum dryer for vacuum microwave drying. The temperature was controlled below 40° C., and the vacuum level was −0.08 Mpa to 0.096 Mpa. A solid was obtained after about 16-19 min of the vacuum microwave drying. The vacuum microwave drying continued for 4-6 min.

The solid was transferred to another vacuum drying oven with a temperature of 34-36° C. After carbon dioxide gas was passed into and out of the vacuum drying oven for about 24 hours, sampling and determination of the content of residual solvent were performed. When the content of residual solvent methanol is not higher than 3,000 ppm, the gas blowing was stopped, and phosphorus pentoxide was placed in the vacuum drying oven which was vacuumed (to make the vacuum level higher than −0.096 Mpa) for further drying. The content of water was monitored. When the content of water was less than 4.0%, the material was taken out, which is the purified rocuronium bromide.

Analysis: the content of water 3.3%; the contents of residual solvents: methanol 1,200 ppm, acetonitrile not detected, methyl tert-butyl ether 960 ppm, and dichloromethane 360 ppm; related substances: A 0.08%, C 0.13%, F 0.05%, G 0.03%, H 0.04%, B, D, and E were not detected, and the total amount of impurities was 0.43% (the upper limit of the qualification standard was 1.5%); and the content was 99.6% (calculated on the anhydrous basis).

Example 4

Preparation of crude rocuronium bromide: 500 g of rocuronium bromide intermediate monoester, 2 L of dichloromethane, and 600 mL of 3-bromopropene were mixed and stirred at room temperature for 16 hours. The reaction solution was filtered, and the filtrate was added to 1 L of dichloromethane. After the mixture was mixed with 25 L of methyl tert-butyl ether while stirring vigorously, a suspension containing a white precipitate was given. After the suspension was stirred for 20 minutes, the precipitate was filtered off, re-dissolved with 3.5 L of dichloromethane, and slowly added to 20 L of ethyl acetate-methyl tert-butyl ether (V:V=1:10) mixed solvent under vigorous stirring to precipitate a white precipitate, which was filtered and mixed with a solvent to obtain a crude rocuronium bromide.

Purifying of crude rocuronium bromide: 600 mL of methanol was added to the crude rocuronium bromide, and then 400 mL of methanol was removed in vacuum at the temperature below 27° C. Then 250 mL of methanol, 90 mL of water, and 30 mL of acetic acid were added to the mixture to make it into liquid which was then added into a microwave tray. The tray containing the stuff was placed in a microwave vacuum dryer for drying. The temperature was controlled below 43° C., and the vacuum level was between −0.08 Mpa and −0.098 Mpa. After about 15-20 min of drying, a solid was obtained.

The solid was transferred to a vacuum drying oven with a temperature which is set at 36° C. After nitrogen was passed into and out of the vacuum drying oven for about 24 hours, sampling and determination of the content of residual solvent were performed. When the content of residual solvent methanol was not higher than 5,000 ppm, the gas drying was stopped, and phosphorus pentoxide was placed in the vacuum drying oven which was connected to a vacuum pump and vacuumed for drying for another 6 hours. Then, sampling and determination of the contents of residual solvent and water were performed. If the sample was not qualified, vacuum drying was continued for 3-5 hours until the sample was qualified. Then, the material was taken out of the oven and pulverized, and passed through a 50-60 mesh sieve to obtain a purified rocuronium bromide.

Analysis: the content of water 3.5%; the contents of residual solvents: methanol 1,900 ppm, dichloromethane 60 ppm, ethyl acetate 960 ppm, methyl tert-butyl ether 830 ppm, and acetic acid 4.6%; related substances: A 0.06%, C 0.1%, F 0.08%, G 0.04%, H 0.05%, B, D, and E were not detected, and the total amount of impurities was 0.39% (the upper limit of the qualification standard was 1.5%); and the content was 99.5% (calculated on the anhydrous and acetic acid-free basis).

Example 5

Preparation of crude rocuronium bromide: 400 g of rocuronium bromide intermediate monoester, 3.6 L of dichloromethane, 150 mL of allyl bromide and 8 g of chitin were mixed and stirred at a temperature of 30-34° C. for 23-25 hours under nitrogen protection. The reaction mixture was filtered, and the filtrate was concentrated under reduced pressure at the temperature of below 26° C. into a viscous state. Then 400 mL of dichloromethane was added to the mixture which was concentrated into a foamy state under the same condition as the above. Purifying of crude rocuronium bromide: 530 mL of methanol was added to the foamy stuff. A flask and the staff therein were weighed. 290 g was distilled off under reduced pressure at the temperature of below 28° C. 230 mL of a methanol-water-acetic acid mixed solvent (V/V/V=4:4:1) was added to the liquid and mixed, which was then added into a microwave tray. The tray containing the stuff was placed in a microwave vacuum dryer for drying. The temperature was controlled below 43° C., and the vacuum level was −0.08 Mpa to −0.098 Mpa. After about 15-20 min of microwave vacuum drying, a solid was obtained.

The solid was transferred to a vacuum drying oven with a temperature which is set at 33-36° C. After a mixture of nitrogen and carbon dioxide (V/V=1:6) was passed into and out of the vacuum drying oven for about 24 hours, sampling and determination of the content of residual solvent were performed. When the content of residual solvent methanol was not higher than 3,000 ppm, the gas blowing was stopped, and phosphorus pentoxide was placed in the vacuum drying oven which was connected to a vacuum pump and vacuumed (to make the vacuum level higher than −0.096 Mpa) for further drying. The content of water was monitored. When the content of water was less than 4.0%, the material was taken out, which is the purified rocuronium bromide.

Analysis: the content of water 3.2%; the contents of residual solvents: methanol 1,600 ppm, dichloromethane 360 ppm, acetic acid 4.1%; HPLC detection: related substances: A 0.08%, C 0.1%, F 0.08%, G 0.03%, H 0.04%, B, D, and E were not detected, and the total amount of impurities was 0.39% (the upper limit of the qualification standard was 1.5%); and the content was 99.6% (calculated on the anhydrous basis).

Example 6

Preparation of crude rocuronium bromide: 400 g of rocuronium bromide intermediate monoester, 3.6 L of dichloromethane, 200 mL of allyl bromide and 8 g of chitin were mixed and stirred at a temperature of 30-34° C. for 22-24 hours under nitrogen protection. The reaction mixture was filtered, the filtrate was concentrated to a foamy state under reduced pressure, 3.6 L of dichloromethane was added to dissolve the foamy solid into a solution, and then the solution was added to 36 L of diethyl ether while stirring. The resulting suspension was stirred for 20 minutes, and a solid was filtered off. The obtained solid was transferred to a vacuum drying oven which was vacuumed at room temperature for 2 hours to obtain a powdery solid. Purifying of crude rocuronium bromide: The solid was transferred to a fluidized bed dryer. A gas at a temperature of 36° C. went through a sulfuric acid absorption device and entered the system to keep the material in a fluidized state. After 24 hours, the residual solvent was determined by gas chromatography. If the content of the residual solvent was not qualified, the drying continued until it was qualified. When the content of the residual solvent was qualified, the content thereof, the related substances and the content of water were measured.

Analysis: diethyl ether 3,300 ppm, and dichloromethane 320 ppm; related substances: impurity A 0.13%, impurity C 0.07%, impurity F 0.1%, and impurities G, D, E, H, and B were less than 0.05%; water 2.3%; the total amount of impurities was 0.61%; and the content of the main component was 99.0% (calculated on the anhydrous).

Example 7

Preparation of crude rocuronium bromide: 400 g of rocuronium bromide intermediate monoester, 3.6 L of dichloromethane, 200 mL of allyl bromide and 8 g of chitin were mixed and stirred at a temperature of 30-34° C. for 22-24 hours under nitrogen protection. The reaction mixture was filtered, the filtrate was concentrated to a foamy state under reduced pressure, 3.6 L of dichloromethane was added to dissolve the foamy solid into a solution, and then the solution was added to 36 L of methyl tert-butyl ether while stirring. The resulting suspension was stirred for 20 minutes, and a solid was filtered off.

Purifying of crude rocuronium bromide: The solid was washed with diethyl ether for 3-4 times, and then transferred to a vacuum drying oven which was vacuumed at room temperature for 2 hours. Then, a powdery solid was obtained. The powdery solid was transferred to a fluidized bed dryer. A gas at a temperature of 36° C. went through a sulfuric acid absorption device and entered the system to keep the material in a fluidized state. After 24 hours, the residual solvent was determined by gas chromatography. If the content of the residual solvent was not qualified, the drying continued until it was qualified. When the content of the residual solvent was qualified, the content thereof, the related substances and the content of water were measured.

Analysis: methyl tert-butyl ether 4,600 ppm, diethyl ether 2,000 ppm, and dichloromethane 320 ppm; related substances: impurities A 0.13%, impurities C 0.08%, impurities F 0.09%, impurities G, D, E, H, and B were less than 0.05%, and the total amount of impurities was 0.69%; the content of water was 2.2%; and the content of main component was 99.3% (calculated on the anhydrous basis).

What is claimed is:

1. A method for purifying crude rocuronium bromide, comprising removing residual solvents in the crude rocuronium bromide by vacuum microwave drying or fluidized drying to meet medicinal requirements, wherein:
   removal of the residual solvents in the crude rocuronium bromide by fluidized drying comprises: fluidized drying crude rocuronium bromide in which diethyl ether is a main residual solvent to obtain purified rocuronium bromide;
   the crude rocuronium bromide in which diethyl ether is the main residual solvent is: (a) a crude rocuronium bromide containing diethyl ether as a main residual solvent or (b) a crude rocuronium bromide containing diethyl ether as a main residual solvent after being treated;
   the crude rocuronium bromide is treated to obtain (b) the crude rocuronium bromide containing diethyl ether as a main residual solvent by a method comprising: dissolving crude rocuronium bromide in a dipolar aprotic solvent that is capable of dissolving rocuronium bromide to prepare a crude rocuronium bromide solution, and mixing the crude rocuronium bromide solution with an anti-solvent to prepare a crude rocuronium bromide solid;
   the anti-solvent is diethyl ether or a solvent other than diethyl ether; and
   the solvent other than diethyl ether is selected from one or more of isopropyl ether, methyl tert-butyl ether, methyl acetate, ethyl acetate, butyl acetate, propyl acetate, cyclohexane, n-hexane, and n-heptane.

2. The method according to claim 1, further comprising using a polar solvent having a high microwave-absorbing ability to replace the residual solvents in the crude rocuronium bromide and then vacuum microwave drying the crude rocuronium bromide containing the polar solvent;
   wherein the polar solvent is selected from one or more of a C1 to C4 monohydric alcohol, a C1 to C3 monobasic acid, acetone, butanone, tetrahydrofuran and water.

3. The method according to claim 1, further comprising mixing a polar solvent having a high microwave-absorbing ability and the crude rocuronium bromide into a liquid containing rocuronium bromide, solidifying the liquid by vacuum microwave drying, and then treating by vacuum microwave drying and/or other drying methods to make the contents of the residual solvents and water meet the medicinal requirements;
   wherein the other drying methods may be selected from one or more of a vacuum drying method, a gas blow-drying method, and a fluidized drying method.

4. The method according to claim 1, wherein the dipolar aprotic solvent is selected from one or more of dichloromethane, acetonitrile, acetone, dimethyl sulfoxide (DMSO), N,N-dimethylformamide (DMF) and N,N-dimethylacetamide.

5. The method according to claim 1, comprising dissolving crude rocuronium bromide in the dipolar aprotic solvent to prepare a crude rocuronium bromide solution, and mixing the crude rocuronium bromide solution and the anti-solvent to prepare a crude rocuronium bromide solid, followed by fluidized drying; wherein:
   when the anti-solvent is diethyl ether, the method comprises dissolving crude rocuronium bromide in the dipolar aprotic solvent to prepare a crude rocuronium bromide solution, mixing the crude rocuronium bromide solution and the anti-solvent to prepare a crude rocuronium bromide solid, followed by fluidized drying;

when the anti-solvent is the solvent other than diethyl ether, the method comprises dissolving crude rocuronium bromide in the dipolar aprotic solvent to prepare a crude rocuronium bromide solution, mixing the crude rocuronium bromide solution and the anti-solvent to prepare a crude rocuronium bromide solid, and washing the crude rocuronium bromide solid with diethyl ether, followed by fluidized drying.

6. The method according to claim 1, wherein the fluidized drying is carried out in a gas, and the gas is selected from one or more of air, argon, nitrogen and carbon dioxide gas.

7. The method according to claim 1, wherein when the anti-solvent is not diethyl ether, the method comprises dissolving crude rocuronium bromide in the dipolar aprotic solvent to prepare a crude rocuronium bromide solution, mixing the crude rocuronium bromide solution with the anti-solvent to prepare a crude rocuronium bromide solid, mixing a polar solvent having a high microwave-absorbing ability with the crude rocuronium bromide solid to form a liquid containing rocuronium bromide, and then vacuum microwave drying the liquid.

8. The method according to claim 2, wherein the polar solvent is selected from one or more of methanol, ethanol, formic acid, acetic acid, acetone, and water;

a vacuum level of the vacuum microwave drying is −0.01 Mpa to −0.1 Mpa; and a temperature of the vacuum microwave drying is 10-60° C.

9. The method according to claim 1, wherein the anti-solvent is methyl tert-butyl ether, methyl acetate, ethyl acetate or n-hexane.

10. The method according to claim 1, wherein a temperature of the fluidized drying is 15-70° C.

11. The method according to claim 1, wherein a temperature of the fluidized drying is 25-45° C.

12. The method according to claim 1, wherein a temperature of the fluidized drying is 30-37° C.

13. The method according to claim 4, wherein the dipolar aprotic solvent is selected from one or more of dichloromethane, acetonitrile, acetone and DMSO.

14. The method according to claim 4, wherein the dipolar aprotic solvent is dichloromethane.

15. The method according to claim 7, wherein the method comprises dissolving the crude rocuronium bromide in the dipolar aprotic solvent to prepare a crude rocuronium bromide solution, mixing the crude rocuronium bromide solution with the anti-solvent to prepare a crude rocuronium bromide solid, mixing the crude rocuronium bromide solid with the polar solvent to form a liquid containing rocuronium bromide, solidifying the liquid by vacuum microwave drying, and then treating the crude rocuronium bromide solid by vacuum microwave drying and/or other drying methods to make the contents of solvents and water meet the medicinal requirements; and wherein the other drying methods may be selected from one or more of a vacuum drying method, a gas blow-drying method, and a fluidized drying method.

16. The method according to claim 8, wherein the polar solvent is methanol, ethanol, solvent combination of methanol and water, solvent combination of ethanol and water, solvent combination of methanol and water and acetic acid, or solvent combination of ethanol and water and acetic acid.

17. The method according to claim 8, wherein the vacuum level of the vacuum microwave drying is −0.06 Mpa to −0.1 Mpa, and the temperature of the vacuum microwave drying is 10-50° C.

18. The method according to claim 8, wherein the vacuum level of the vacuum microwave drying is −0.08 Mpa to −0.099 Mpa; and the temperature of the vacuum microwave drying is 10-40° C.

19. The method according to claim 8, wherein the temperature of the vacuum microwave drying is 30-40° C.

20. The method according to claim 8, wherein the temperature of the vacuum microwave drying is 25-36° C.

* * * * *